US00PP07996P

United States Patent [19]

Moore

[11] Patent Number: Plant 7,996

[45] Date of Patent: Oct. 6, 1992

[54] FLORIBUNDA ROSE PLANT NAMED 'MORPLATI'

[75] Inventor: Ralph S. Moore, Visalia, Calif.

[73] Assignee: Sequoia Nursery, Visalia, Calif.

[21] Appl. No.: 646,263

[22] Filed: Feb. 28, 1991

[51] Int. Cl.[5] ..... A01H 5/00

[52] U.S. Cl. ..... Plt./29

[58] Field of Search ..... Plt./22, 28, 29

*Primary Examiner*—Howard J. Locker

[57] ABSTRACT

This invention relates to a new and distinct variety of rose plant of the Floribunda class, primarily identified by its large single (5 petal) flowers with the petals being bright red orange.

1 Drawing Sheet

1

The present invention relates to a new and distinct variety of hardy, bush type rose plant of the Floribunda class; the variety being primarily characterized — as to novelty — by the very single (5 petals) flowers, the petals being generally bright orange red.

The variety is further characterized by:

An abundance of blooms, with flowers usually borne singly, but also several to the stem in loose clusters or sprays. Sepals: permanent; spear shaped; recurved.

Little fragrance.

A plant which is vigorous, of rounded to upright shape with large semi-glossy foliage with pointed leaflets; the buds and flowers being similar in form to Dainty Bess (not patented).

The plant, which has a normal height of 3–4 feet, can easily be maintained at lesser height by occasional trimming.

A plant which grows and blooms satisfactorily both in greenhouse and outdoors; is good for growing in the garden or large pot; and provided excellent garden decoration as well as cut flowers.

The present variety of floribunda rose was originated by me at my nursery, located at Visalia, Calif., under conditions of careful control and observation, as a cross between Playboy (floribunda, not patented), as the seed parent and Old Master (floribunda, not patented) as the pollen parent.

Subsequent to origination of the variety I successfully asexually reproduced it at the same nursery, located as aforesaid, by budding as well as by cuttings; the reproductions having run true in all respects.

The color photograph illustrates the variety including the foliage, buds and flowers.

Referring now specifically to the new and distinct variety of floribunda rose plant, the following is a detailed description thereof in outline, all major color plate identifications being by reference to the British Colour Council Horticultural Colour Chart, except where common terms of color definition are employed.

Type: Hardy; bushy; upright; seedling; outdoors; cut flowers; garden decoration.

Class: Floribunda.

*Variety identification.*—MORplati.

*Commercial synonym.*—PLAYTIME.

Flowers borne: Singly and several together in loose clusters or sprays on sturdy, wirey stems.

Quantity of bloom: Abundant.

Bud:

2

*Peduncle.*—Medium to long length; slender but sturdy; erect; medium green, sometimes tinted bronze (outdoors); nearly smooth or with some very small hair-like appendages.

*Before calyx breaks.*—Size — medium. Form — long pointed, with several small foliaceous appendages on surface of bud; with foliaceous parts extending beyond the tip of the bud equal to more than one-half of its length. Color — medium green, occasionally tinted with bronze (outdoors).

*As calyx breaks.*—Color — red (near Cardinal Red 822 or 822/1) with sometimes deeper blackish shading at petal tip.

*Opening.*—Opens well in all weather.

Bloom:

*Size when fully open.*—Small, averaging about 8–9 cm (3½").

*Petalage.*—Single, 5 large petals, arranged regularly (one row of petals).

*Form.*—Open to flat. Open flowers have stamens.

Petals: Fairly thick; satiny on inside and on outside surface.

*Shape.*—Outside petal — broad lanceolate (wedge shape) with pointed tip; intermediate — none.

Color: Newly opened flower from a plant grown outdoors (October, 1990), Visalia, Calif.:

*Outside petal.*—Outside surface — deep red (near Cardinal Red 822/1). Inside surface — near Oriental Red 819/2 shading darker (blackish) red at petal edges.

*Intermediate petal.*—None.

*Inner petal.*—None.

*General color effect.*—Newly opened flowers — bright orange red (Oriental red). Three days open — color — similar to fresh open flower, but less bright.

Behavior: Opens well in all weather. Spent petals drop off.

Flower longevity (September–October 1990): Plant in pot or ground 5–7 days or longer. Cut flowers at living room temperature 3–5 days or longer.

Reproductive organs:

*Stamens.*—Abundant.

*Filaments.*—Many.

*Anthers.*—Many.

*Pollen.*—Abundant.

*Pistils.*—Average number.

*Styles.*—Short to medium length; reddish; bunched.

*Ovaries.*—All enclosed in calyx.

*Hips.*—Flattened apple-shaped; generally wider than long; less than average in number.

*Seed.*—Average 4–5 per hip.

Foliage:

*Leaves.*—Compound of five (sometimes three or seven) leaflets: large; leathery; semi-glossy.

*Leaflets.*—Shape — broad lanceolate; apex acute; base — usually rounded. Color: medium green; new growth — normal (medium) green (sometimes tinted reddish).

*Rachis.*—Medium strength; nearly smooth with sometimes a few short fuzzy hairs; grooved; underside may have several small thorns (or claws) and few to several tiny short prickles.

*Stipules.*—Medium to short length; medium to narrow width; narrow points which turn out usually at about 45 degrees or more.

Growth:

*Habit.*—Bushy; upright; much branched.

*Growth.*—Vigorous; internodes average.

*Canes.*—Medium; slender; sturdy.

*Main stems.*—Color: medium green.

*Thorns.*—Few to average, of varying size and length — slender with sharp points, slightly inclined downward.

*Hairs.*—Few or none.

The floribunda rose plant and its flowers as herein described may vary in slight detail due to climatic, soil and cultural conditions under which the variety may be grown; the present description being of the variety as grown at Visalia, Calif.

The following is claimed:

1. A new and distinct variety of floribunda rose plant of hardy, bushy, upright, much branched habit, substantially as illustrated and described, characterized by buds and flowers, resembling the Dainty Bess cultivar in form and size, the open flower (upper surface) being near Orient Red 819/2 in color with the reverse side being near Cardinal Red 822/1, the flowers, generally having only five broad petals, being borne singly and in loose clusters; and further characterized by the plant being easy to propagate from soft wood cuttings or by budding, with an abundance of large semi-glossy foliage.

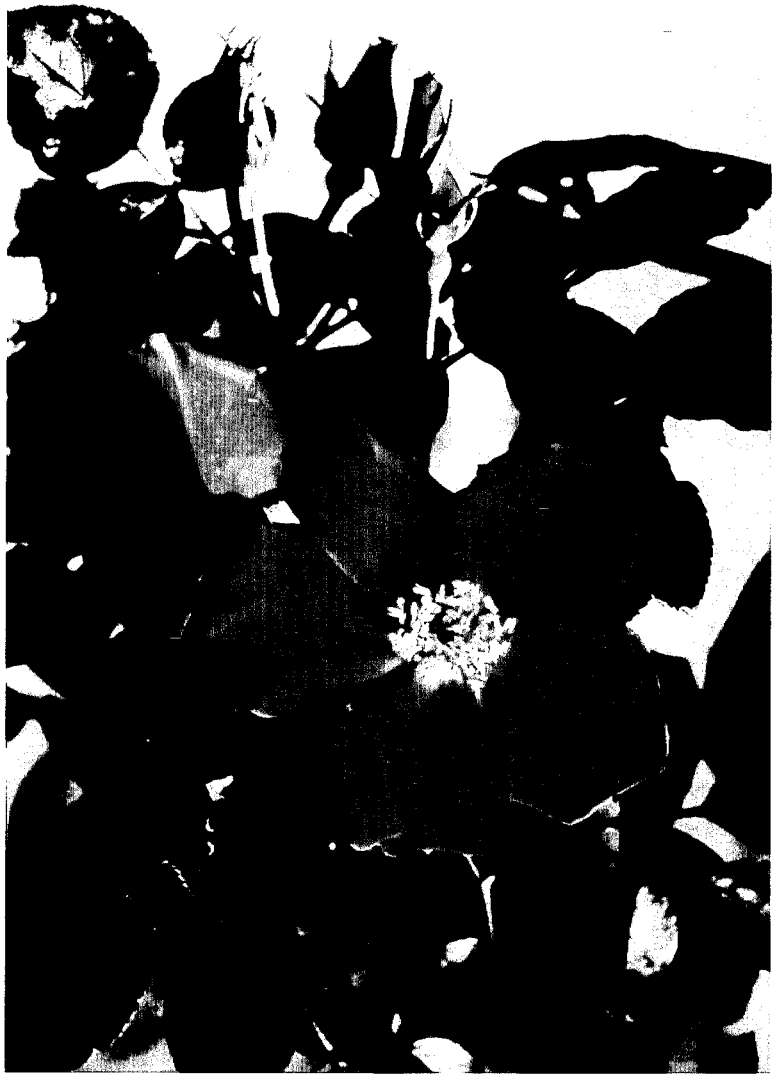

* * * * *